United States Patent [19]

Johnston

[11] 4,080,821
[45] Mar. 28, 1978

[54] ELECTRIC CIRCUITS

[75] Inventor: James Stewart Johnston, Bognor Regis, England

[73] Assignee: Rosemount Engineering Company Limited, Bognor Regis, England

[21] Appl. No.: 781,764

[22] Filed: Mar. 28, 1977

[51] Int. Cl.² .............................................. G01F 1/68
[52] U.S. Cl. ..................................... 73/27 R; 73/204
[58] Field of Search ............. 73/27 R, 204; 323/75 B, 323/75 H

[56] References Cited
U.S. PATENT DOCUMENTS

| 2,552,017 | 5/1951 | Schwartz et al. | 73/204 |
| 2,726,546 | 12/1955 | King, Jr. | 73/204 |
| 3,995,481 | 12/1976 | Djorup | 73/204 |

Primary Examiner—Herbert Goldstein
Attorney, Agent, or Firm—Dugger, Johnson & Westman

[57] ABSTRACT

An electric circuit includes three matched resistance thermometer sensors and is responsive to changes in rate of heat loss from at least one of them. The sensors are connected in a series-parallel arrangement to form one arm of a bridge circuit. An amplifier detects imbalance in the bridge and controls current flowing in the bridge to restore balance. Twice as much current flows in one sensor than in the other two, so that the one is maintained hotter. Environmental changes effecting a change in the rate of heat loss from the one sensor are detected as a change in current flowing in the bridge.

15 Claims, 5 Drawing Figures

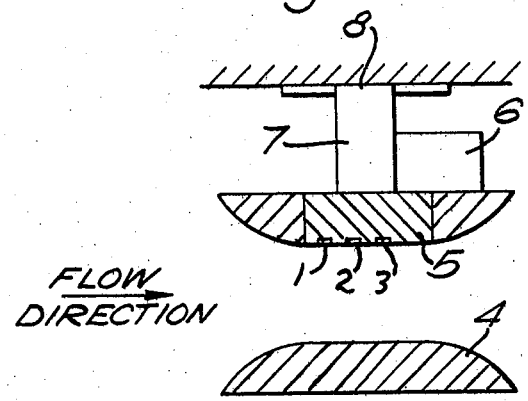
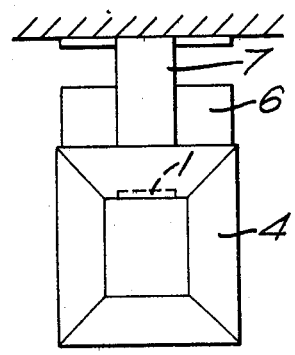
Fig. 1a. Fig. 1b.
FLOW DIRECTION
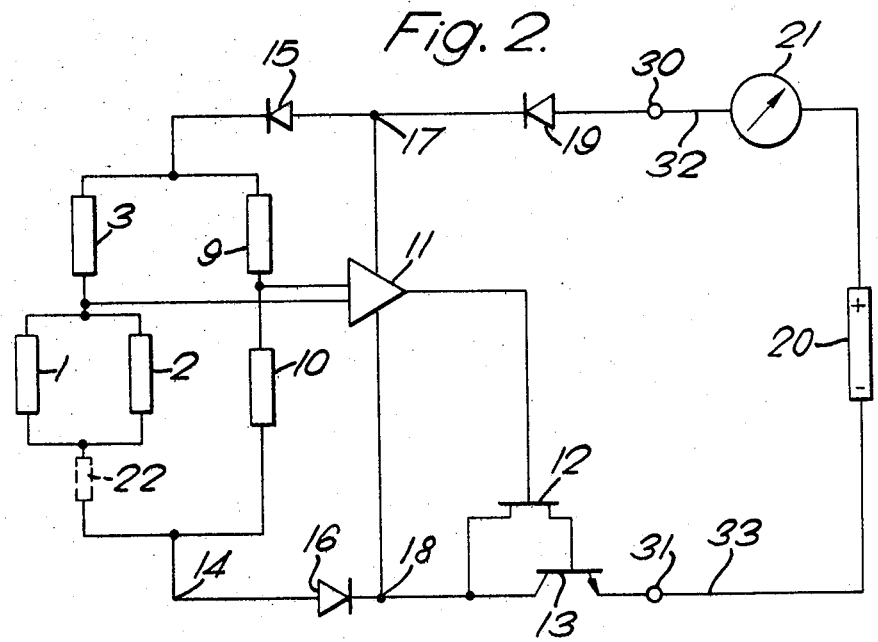
Fig. 2.

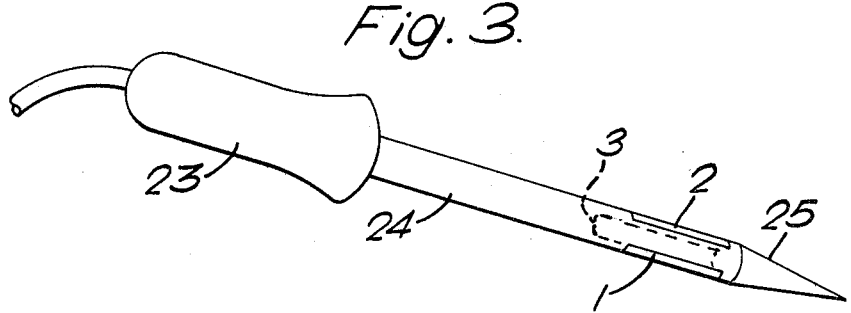
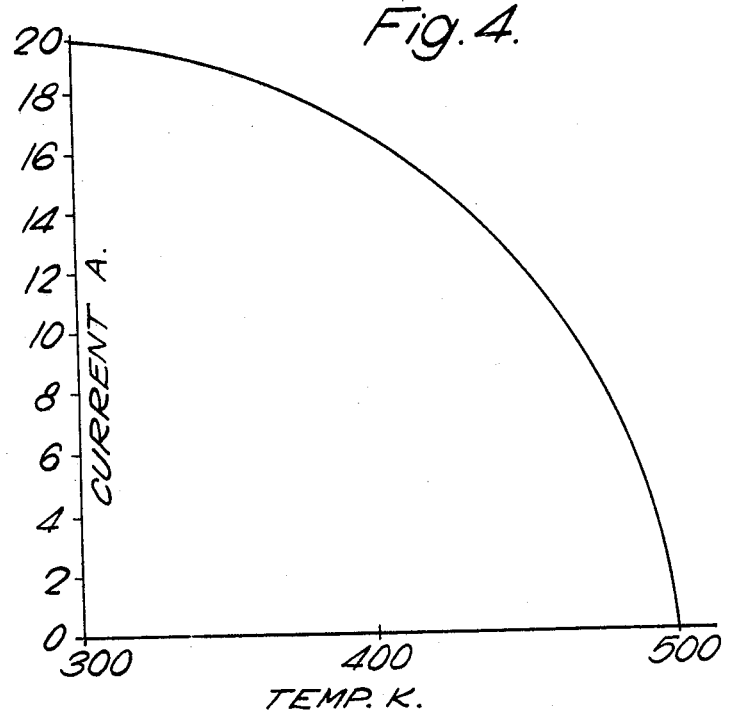

ELECTRIC CIRCUITS

The present invention relates to electric circuits and in particular to circuits which are responsive to changes in the rate of heat loss from a resistance thermometer sensor. Circuits of this kind can be used for determining the rate of flow of a fluid. A resistance thermometer sensor is supported in a stream of the fluid and a current is passed through the sensor to heat it to a temperature somewhat above that of the fluid. If the fluid flow rate increases, the rate of loss of heat from the sensor will also increase causing a drop in the temperature of the sensor. If the sensor is connected in a suitable electric circuit, the drop in resistance of the sensor corresponding to this drop in temperature can be detected and hence an indication of the flow rate of the fluid can be obtained. Alternatively, the flow rate may be inferred from the extra heating current in the sensor required to prevent such a resistance drop.

In order to make the sensing circuit independent of the temperature of the fluid flowing, it is usual to provide a second reference resistance thermometer sensor. The two sensors are then included in a circuit which is designed to respond only to the change in the ratio of the resistance values of the two sensors.

According to the present invention an electric circuit responsive to changes in the rate of heat loss from a resistance thermometer sensor comprises a bridge circuit having first and second arms connected in parallel, the first arm comprising a first resistance thermometer sensor and second and third resistance thermometer sensors connected in parallel with each other and connected at a first balance point in series with said first resistance thermometer sensor, the three resistance thermometer sensors having closely matched values, the second arm comprising first and second resistances connected in series at a second balance point, and a differential amplifier having its inputs connected between the first and second balance points and having its output connected to control current flow in the bridge circuit, the arrangement being such that the differential amplifier is operative to balance the bridge circuit with a finite current flowing in said resistance thermometer sensors.

References above and elsewhere herein to the three resistance thermometer sensors having 'closely matched values' are intended to convey that the parameters, icepoint resistance and temperature coefficient of resistance, of the three sensors are substantially similar. It is important that the sensors are closely matched in this way to ensure that the circuit of the invention can be substantially independent of variations in the ambient temperature or so that it can be made to have a predetermined temperature dependance as will become apparent. The closeness of matching required for performing the present invention is dependent on the particular application. If the circuit is to be very sensitive and to be used over a wide range of ambient temperatures, the matching must be closer than if low sensitivity is required in nearly constant temperature conditions.

It can be seen that, if the three resistance thermometer sensors in the above circuit are at the same temperature, the bridge circuit is balanced if the first and second resistances have relative values in the ratio 2 : 1. However, the finite current flowing through the resistance thermometer sensors causes resistive heating. The current flowing in said first resistance thermometer sensor is twice that flowing in each of said second and third resistance thermometer sensors. Thus, the heat dissipation in said first resistance thermometer sensor will be four times that in each of said second and third sensors. Thus, if all three sensors are exposed to the same or similar cooling environments, the temperature of said first resistance thermometer sensor will be higher than that of each of said second and third resistance thermometer sensors. It can be seen therefore that, to balance the bridge with a finite current flowing through the resistance thermometer sensors, said first resistance may have a value fractionally greater than twice the value of said second resistance. With this arrangement the circuit is substantially independant of ambient temperature. However, instead or as well, a third resistance may be provided in series with said parallel connected second and third resistance thermometer sensors, the value of said third resistance being a fraction of the ice point resistance value of said second and third resistance thermometer sensors connected in parallel. This third resistance introduces a predetermined degree of temperature dependance which may be desirable in some applications. With each arrangement, the differential amplifier controls the current flowing in the bridge circuit so that said first resistance thermometer sensor is at a suitable temperature to balance the bridge.

If the rate of heat loss from said first resistance thermometer sensor changes, causing the sensor to become warmer or cooler, the circuit responds to reduce or increase the current flowing in the bridge to restore balance. Thus, the circuit responds to changes in the rate of heat loss from the first resistance thermometer sensor and the current flowing in the bridge is representative of this rate of heat loss.

Preferably the values of the first and second resistances are more than five times the ice point resistance of each of the three resistance thermometer sensors. Then the greater part of the current flowing in the bridge flows through the resistance thermometer sensors and there is relatively little wasteful power dissipation in said first and second resistances.

For proper operation of the circuit the input impedence of the differential amplifier should be high compared with the values of any of the resistance values in the bridge circuit.

Preferably, the circuit includes means for connecting a direct voltage supply across the bridge circuit and current control means in series with said connecting means and connected to the output of said differential amplifier whereby to control current flowing in said connecting means to said bridge circuit. Then, the differential amplifier may have at least one power supply connection to said connecting means between said current control means and the bridge circuit.

The connecting means may include a pair of terminals for connection to a source of direct voltage, so that the bridge circuit, the differential amplifier, the connecting means and the current control means together constitute a two-wire transmitter. A two-wire transmitter is an electrical signalling device requiring the connection of only two wires to provide both a power supply to the device and a signalling line from the device to a remote point. The signals appear as current variations in the power lines. It can be seen that this preferred embodiment of the present invention constitutes a two-wire transmitter since it is only necessary to connect a power supply across said pair of terminals to activate the circuit. The differential amplifier then takes its power from the connected supply. However, the current requirement of a suitable differential amplifier is small compared with the current flowing in the bridge circuit required to balance the bridge. Therefore, the current drawn from the supply by the circuit will be representative of the rate of heat loss from said first resistance thermometer sensor.

Accordingly, the invention further envisages the provision of a direct voltage power supply and a current meter in series therewith, remote from said two-wire transmitter, and a two-wire connection from said power supply and current meter to said pair of terminals.

It is especially convenient that the three resistance thermometer sensors each comprise a conductive platinum rich vitreous film deposited on an insulating substrate. Such a sensor may be formed as an elongate rectangular chip. Such flat deposited film devices can be produced relatively cheaply with close tolerance ice point resistance values. Also, such flat film devices can have relatively low thermal capacities and may respond relatively quickly to changes in ambient temperature or cooling conditions. Thus, when employed in the circuit of the present invention, the flat film sensors respond quickly producing a correspondingly quick change in the current required to rebalance the bridge.

In one application of the circuit of the present invention, apparatus for measuring fluid flow rate comprises the circuit in combination with means for exposing the three resistance thermometer sensors correspondingly to a flowing fluid of which the flow rate is to be measured. The rate of loss of heat of the sensors depends on the rate of flow of the fluid. Since said first sensor is at a higher temperature than said second and third sensors, a change in the rate of flow of fluid cools said first sensor more than said second and third sensors, unbalancing the bridge and requiring a corresponding change in the current flowing in the bridge to rebalance it. Thus, the current flowing in the bridge is representative of the rate of flow of fluid. So that the circuit is independant of ambient temperature in this application, the arrangement is used in which the first resistance has a value fractionally greater than twice the value of the second resistance, and no third resistance is provided as described previously.

Conveniently said means for exposing comprises a rectangular venturi adapted to be located in the fluid stream, the three sensors being mounted so as to be flush with an interior surface of the venturi. Preferably, the sensors are mounted in a material of low thermal conductivity so that relatively little heat is lost from the sensors by conduction through the body of the apparatus.

In another application of the circuit of the present invention, an apparatus for determining changes in the thermal conductivity of a gas comprises said circuit in combination with means for exposing the three resistance thermometer sensors correspondingly to the gas. Then, the current required to balance the bridge will depend on the thermal conductivity of the gas. This apparatus is especially useful for determining the concentration of one gas in another, where the two gases have different thermal conductivities. In order to minimise the effect on the apparatus of changes in thermal conductivity of the gas or the gas mixture with temperature, said third resistance is provided in series with parallel connected second and third resistance thermometer sensors and said first and third resistances have values selected to minimize the temperature dependence of the apparatus. A theoretical explanation of how suitable values may be chosen is given later herein.

There now follows a description of various examples of the invention together with the various applications. The description makes reference to the accompanying drawings in which:

FIG. 1a and 1b are side view and front views respectively of a fluid flow rate measuring apparatus incorporating a circuit in accordance with the present invention;

FIG. 2 is a schematic diagram of a circuit responsive to changes in the rate of heat loss from a resistance thermometer sensor;

FIG. 3 illustrates a probe for determining the thermal conductivity of solid materials and FIG. 4 is a graphical plot of current against absolute temperature illustrating operation of an apparatus incorporating a circuit in accordance with the present invention and used as a radiation pyrometer.

Referring firstly to FIG. 2, there is illustrated diagrammatically a circuit which is responsive to changes in the rate of loss of heat from a resistance thermometer sensor. A bridge circuit has a first arm comprising a first resistance thermometer sensor 3 connected in series with second and third resistance thermometer sensors 1 and 2, which are connected in parallel with each other. The bridge circuit has a second arm comprising a first resistance 9 in series with a second resistance 10. The two arms of the bridge circuit are connected in parallel. A differential amplifier 11 has one input connected to the connection point between the first resistance thermometer 3 and the parallel connected resistance thermometers 1 and 2 and has a second input connected to the connection point of the two resistances 9 and 10. Thus, the connection point of the sensor 3 with the parallel connected sensors 1 and 2 constitutes a first balance point of the bridge and the connection point of the two resistances 9 and 10 constitute a second balance point of the bridge.

A direct voltage is applied across the bridge circuit by a power supply 20 which is connected in series with a current meter 21. The meter 21 is connected to one side of the bridge circuit via a forward biased protection diode 19 and a further forward biased diode 15. The negative terminal of the power supply 20 is connected to the other side of the bridge circuit via a current controlling arrangement and a forward biased diode 16.

The current controlling arrangement comprises the emitter collector circuit of a junction transistor 13, the current flowing in which is controlled by a field effect transistor 12 with its drain source circuit connected between the base and collector of the junction transistor 13. The output of the differential amplifier 11 is connected to the gate of the field effect transistor 12. Thus, the current flowing in the bridge circuit is controlled in accordance with the output of the differential amplifier 11.

The power supply for the amplifier 11 is taken from points 17 and 18, point 18 being between the transistor 13 and the bridge circuit. The diodes 15 and 16 serve to provide additional voltage drop so that there is sufficient supply voltage between points 17 and 18 to operate the amplifier 11. Diode 19 protects the circuit from the effects of inadvertent reversal of the power supply connections.

In some applications of the circuit of FIG. 2, a third resistance 22 is provided in series with the parallel connected sensors 1 and 2. Normally the value of the third resistance 22 is a fraction of the ice point resistance value of the parallel connected sensors 1 and 2.

Further details of the circuit of FIG. 2 will become apparent from the following descriptions of applications of the circuit. In these applications, the three resistance thermometer sensors 1, 2 and 3 are formed as deposited vitreous conductive films on insulating substrates. Such films may be formed by printing a suitable substrate of, for example, alumina with an ink of glass and platinum metal particles. The printed substrate is then dried and fired to form the vitreous conductive film which has similar temperature dependent characteristics to platinum metal. The substrate and film is usually then provided with a protective glass coating. The complete sensor has, typically, the shape of an elongate rectangle.

In a first application, the circuit of FIG. 2 may be employed in a flow meter such as that illustrated in FIGS. 1a and 1b, which show these three resistance thermometer sensors 1, 2 and 3 mounted so as to be flush with an internal wall of a rectangular venturi 4. The flat profile of the above described deposited film sensors enables them to be mounted in the wall of the venturi with the printed faces of the sensors flush with the wall and exposed to the interior of the venturi. The sensors are mounted in a region 5 of the venturi formed of a material having a low heat conductivity so that the sensors are substantially heat insulated from the body of the venturi. The venturi is mounted by means of a strut 7 from the wall 8 of a duct or similar device in which the rate of fluid flow is to be monitored. The sensors 1, 2 and 3 are connected to the rest of the circuit of FIG. 2 which is contained in an enclosure 6 mounted on the venturi 4.

In the venturi illustrated in FIGS. 1a and 1b, the sensors 1, 2 and 3 are mounted with their long axes transversely across the flow direction. However, the sensors may alternatively be mounted with their long axes substantially aligned with the flow direction. In that case, the sensors may be mounted in the walls of a venturi with a circular cross section. Then the sensors are preferably mounted side by side at circumferentially spaced positions about the venturi.

Referring again to the circuit of FIG. 2, the sensors 1, 2 and 3 have ice point resistances ($R_o$) and temperature coefficients of resistance ($\alpha$) which are closely matched. It can be seen, therefore, that in order to obtain a balanced bridge when all the sensors are at the same temperature, the value ($R_1$) of the first resistance 9 should be equal to twice the value ($R_2$) of the second resistance 10. However, $R_1$ is made slightly greater than this value so that:

$$R_1 = 2 R_2 + \alpha R_1 \tag{1}$$

(in this example, the value ($R_3$) of the third resistance 22 is zero).

Also, $R_1$ is made much greater than, at least five times, the resistance value ($R_T$) of each resistance thermometer sensor at the ambient temperature T. Considering the situation where a small current $i$ is flowing in a line 14, i.e. through the bridge circuit, the bridge will be unbalanced, where the current $i$ is insufficient to cause significant heating in the resistance theremometer sensors. The unbalanced voltage $Vb$ is given approximately by $$Vb \approx i \, \Delta R_1 \cdot (R_T/R_1) \tag{2}$$

This unbalanced voltage is amplified by amplifier 11 causing the field effect transistor 12 to switch on the junction transistor 13 to conduct a larger current. Substantially, the whole of current $i$ flows in the arm of the bridge containing the resistance thermometer sensors, since the resistance of the other arm is much greater. This increased current causes heating of the sensors 1, 2 and 3 but the heating effect in sensor 3 is four times that in sensor 1 or sensor 2 since only half the current flows in sensors 1 and 2 and the heating effect is proportional to the square of the current. Thus, the resistance of sensor 3 is increased relatively to the resistances of sensors 1 and 2, so tending to rebalance the bridge. The amplifier 11 has a high gain so that the circuit will operate to maintain the bridge substantially in balance with $Vb$ substantially zero.

The current in line 14 needed to keep the sensor 1 a few degrees hotter than its surroundings is given approximately by $$i = (\Delta R_T/R_T)^{\frac{1}{2}} \cdot (kA + B\sqrt{kV})^{\frac{1}{2}} \tag{3}$$

where $\Delta R_T$ is the increase in sensor resistance equivalent to the temperature rise above the surroundings,
$k$ is the thermal conductivity of the fluid to which the sensors are exposed,
V is the flow velocity of the fluid, and A and B are constants.

The circuit of FIG. 2 operates so that $$\Delta R_T/R_T = \Delta R_1/R_1 \tag{4}$$

so that $(R_T/R_T)^{\frac{1}{2}}$ is constant.
If the thermal conductivity of the fluid is constant, $$i = C(D + \sqrt{V})^{\frac{1}{2}} \tag{5}$$

where C and D are constants.

Although the above equations are strictly applicable only to cylindrical bodies fully exposed to the flow, in practice they are followed reasonably well by the deposited film sensors mounted in the wall of the venturi as indicated in FIG. 1.

In a particular experiment using air as the fluid and choosing a value of $R_1$ to give a temperature rise of about 2.5° C for the sensor 3, the current $i$ at zero flow velocity was 10 milliamps, increasing to 20 milliamps at a flow rate of 5 meters per second.

It can be seen that the circuit adusts the current $i$ to be sufficient to heat the sensor 3 a few degrees Celsius above the local ambient temperature. This current is thus a measure of the heat loss from the sensor 3 and the circuit responds to variations in this rate of heat loss. Since the heat loss is dependent on the flow velocity of a fluid past the sensor, the current is representative of this flow velocity.

The amplifier 11 has relatively small power requirements and thus the current drawn from the power supply 20 as measured by the current meter 21 is substantially the same as current $i$ flowing in line 14. In a practical embodiment, the power supply 20 and meter 21 are situated remotely from the rest of the circuit of FIG. 2 connected thereto by wires 32 and 33 connected to terminals 30 and 31 Thus, the circuit comprising the bridge, the amplifier 11 the transistors 12 and 13 together with the terminals 30 and 31 constitute a two-wire transmitter, requiring only the connection of the two-wires 32 and 33 both for power supply for the circuit and as signalling wires.

The construction of flow meter illustrated in FIGS. 1a and 1b is especially convenient because it can be easily cleaned, does not significantly restrict the fluid flow, is robust and is not damaged or effected by the presence of dust in a gaseous fluid. The use of deposited film type sensors as sensors 1, 2 and 3 overcomes the problems of the varying internal heat transfer properties which are typical of conventional types of sensors. The good thermal contact between the film and the substrate of the sensors allows the sensors to respond quickly and precisely to relatively small variations in ambient temperature or rate of cooling. Because of the above increased precision of deposited film type sensors, their use enables the circuit of FIG. 2 to operate with relatively low voltages so that the flow meter including the circuit can be considered intrinsically safe. Thus, the flow meter with printed film type sensors is especially useful in hazardous environments such as for measuring air flow rates in coal mines, or measuring the flow rate of hydrogen gas.

The construction of flow meter illustrated in FIGS. 1a and 1b is not essential. In some cases, it may be preferable to mount the sensors 1, 2 and 3 directly in the surface of a pipe or duct in which the fluid is flowing without reducing the cross sectional area to form a venturi. In other cases, particularly in very small pipes or ducts, the sensors may be suspended in the pipe without being mounted in a supporting medium. However, in such a case the advantage of easy cleaning of the sensors is lost.

In another application the circuit of FIG. 2 can be used for measuring the thermal conductivity of a gas, or gas mixture. There are significant differences in the thermal conductivities of different gases so an instrument which provides an output representative of the thermal conductivity of a gas can be used to measure the concentration of one gas in another, or to detect the presence of small quantities of one gas in another, From the equation (3) above, with zero flow velocity, $$i = \left( \frac{\Delta R_T}{R_T} \cdot kA \right)^{\frac{1}{2}} \quad (6)$$

It is important that the sensors are suspended in the gas so as to avoid a significant proportion of the heat being lost by conduction in the supports or wall material and also it is important to ensure that there is no significant flow of gas across the sensors.

The thermal conductivity of gases rises with increasing temperature so there is a danger that variations in gas temperature may mask or be mistaken for, changes in the gas composition, i.e. thermal conductivity. This danger can be avoided or minimized if the quantity $(\Delta R_T/R_T) \cdot k$ is arranged not to vary with the temperature of the gas.

Over the normal ambient temperature range, the thermal conductivity of most gases can be represented by $$k_t = k_o(1 + \beta t)$$

where $k_t$ is the thermal conductivity at $t°$ C, $K_o$ is the thermal conductivity at $0°$ C and $\beta$ is a constant. For air and other gases remote from their critical points, $\beta$ is approximately equal to 0.00315. In the case of more readily condensible gases and vapours the value is higher (e.g. 0.0048 for carbon dioxide).

In the circuit described above, with $R_3$ equal to 0, the quantity $\Delta R_T/R_T$ has no temperature coefficient since it is equal to $\Delta R_1/R_1$. If, however, the circuit is changed so that $\Delta R_1 = 0$ (i.e. so that $R_1 = 2R_2$) and the third resistance 22 is given a finite value $R_3$, the bridge will balance when the resistance of sensor 3 exceeds that of sensors 1 or 2 by an amount $2R_3$. In this case $\Delta R_T = 2R_3$ and equation (6) above becomes $$i = \left( \frac{2R_3}{R_T} \cdot kA \right)^{\frac{1}{2}} \quad (7)$$

or $$i = \left( \frac{2R_3}{R_o(1 + \alpha t)} \cdot k_o(1 + \beta t)A \right)^{\frac{1}{2}} \quad (8)$$

where $\alpha$ is the temperature coefficent of resistance of the sensors 1, 2 and 3.

Ideally, when $\alpha = \beta$, the current $i$ is not a function of temperature. In practice, the value of $\alpha$ for a platinum resistor is 0.00385 which lies between the value of $\beta$ for air and other permanent gases and the values appropriate to condensible gases.

Where the apparatus is used to detect the presence of small quantities of one gas in another gas, (typically air), it is more important to arrange that the device does not respond to temperature changes in the major constituent of the mixture, i.e. air. This can be achieved by reintroducing the resistance $\Delta R_1$ so that the bridge is balanced with $$\Delta R_T = \left( 2R_3 + \frac{\Delta R_1}{R_1} \cdot R_T \right) \quad (9)$$

i.e. $\Delta R_T = 2R_3 + \frac{\Delta R_1}{R_1} \cdot R_o(1 + \alpha t) \quad (10)$ If $R_4 = \frac{\Delta R_1 R_o}{R_1}$, $$\Delta R_T = (2R_3 + R_4)\left(1 + \frac{R_4}{2R_3 + R_4} \alpha t\right) \quad (11)$$

Thus, the temperature coefficient $((R_4/2R_3+R_4) \cdot \alpha)$ of $\Delta R_T$ can be varied from zero (if $R_4$ is zero and hence $\Delta R_1$ is zero) to $\alpha$ (if $R_3$ is zero). This enables the effective temperature coefficient of the ratio $\Delta R_T/R_T$ to be adjusted to match the temperature coefficient of the conductivity $k$ of the gas to be measured, provided $k$ lies in the range zero to 0.00385.

Where the apparatus is used to detect the presence of other gases in air, the values of $R_3$ and $\Delta R_1$ can be chosen so that the current $i$ is independent of the temperature of the air. Then changes in current $i$ must be caused by the introduction of another gas. The change in current $i$ will depend on the difference between the thermal conductivity of the gas introduced and that of air. The extreme may be illustrated by considering an instrument adjusted to draw 10 milliamps in air. With the sensors in sulphur dioxide the current is reduced to 5.7 milliamps and with them in hydrogen, the current rises to 26.7 milliamps.

Particular applications of the above described technique are for monitoring hydrogen/nitrogen mixtures in steel processing, or the composition of cracker or reformer gas, for oxy-hydrogen flame control, or for monitoring carbon dioxide concentration in fruit storage and in crop cultivation.

The application of the circuit in measuring thermal conductivity is not limited to gases. The three sensors 1, 2 and 3 may be secured so as to be flush with the surface of a probe as shown in FIG. 3. The sensors are mounted in a thermally insulating stem 24 of the probe which has a handle 23 and a steel tip 25. The probe can then be inserted into various materials to obtain an indication of thermal conductivity. For example, the probe might be used to measure the moisture content of sand or soil, the freshness of meat or fish, the texture of bread or cakes etc. In some of these applications the transient changes of current $i$ on insertion into the material may also give information on composition or character of the material.

In a further application, the circuit may be used as a radiation pyrometer. If sensors 1 and 2 are arranged so that radiant heat from some source falls on them, but not on sensor 3, the bridge will become unbalanced, requiring an increase in current i to rebalance by increasing the temperature of sensor 3 correspondingly. This method would, however, result in relatively slow response times, since the temperature of the sensors 1, 2 and 3 is changed when exposed to the radiation. A better alternative is to allow the radiant heat to fall on sensor 3 and not on sensors 1 and 2. The result would be a decrease in current $i$ as the radiant energy increases, leaving the temperature of the sensor 3 unchanged. Assuming the temperature of the radiation pyrometer to be 300° k, the current $i$ will follow a law of the form:

$$i = \sqrt{a - b(T^4 - 300^4)}$$

where $a$ and $b$ are constant and T is the temperature of the source of radiation in degrees Kelvin. A typical plot of such a function is shown in FIG. 4.

One way of arranging that the radiation does not reach sensors 1 and 2 is to coat them with a highly reflective material, while sensor 3 is coated with a highly absorbing material.

In a still further application, the circuit of FIG. 2 may be used as the detection system in an infra-red analyser by arranging that, for example, the measurement beam falls on sensor 3 and the reference beam on sensors 1 and 2. Alternatively, sensor 3 and sensors 1 and 2 may be coated with materials having different spectral absorption bands while being irradiated with broad band infra-red irradiation. Interposing a gas (or transparent liquid or solid) between the source and the sensors, which has significantly different absorptions in the bands appropriate to the two coating materials, will cause a bridge unbalance and a compensating change in current $i$. If it is required to "chop" the incident radiation with a sectored disc, the circuit can be arranged to have a frequency response extending to several Hertz.

In a still further application, the circuit may be used as a level detector, in which case the three sensors are arranged to become immersed when the liquid reaches a certain level. It will be understood that the current $i$ of the circuit will be relatively low when the sensors are in air and will rise abruptly when the sensors are immersed.

Since the thermal conductivity of a gas becomes a function of pressure below a few millimeters of mercury, the thermal conductivity meter described above can be used as a vacuum gauge, for example, as an alternative to the Pirani gauge. The thermal conductivity meter can also be used as the detecting element in gas chromatographs.

The above described thermal flow meter can be used as the detector in specific gravity meters based on gravitational separation of a gas flow into upper and lower streams. In general, the circuit described responds to any change in the heat transfer characteristics effecting all the sensors at once or any one of them. The circuit may therefore be used to respond to such things as changes in the evaporation rate of a liquid coating or to exothermic or endothermic reactions on the surface of the sensors, for example assisted by catalytic coatings.

I claim:

1. An electric circuit responsive to changes in the rate of heat loss from a resistance thermometer sensor, the circuit comprising a bridge circuit having first and second arms connected in parallel, the first arm comprising a first resistance thermometer sensor and second and third resistance thermometer sensors connected in parallel with each other and connected at a first balance point in series with said first resistance thermometer sensor, the three resistance thermometer sensors having closely matched values, the second arm comprising first and second resistances connected in series at a second balance point, and a differential amplifier having its inputs connected between the first and second balance points and having its output connected to control current flow in the bridge circuit, the arrangement being such that the differential amplifier is operative to balance the bridge circuit with a finite current flowing in said resistance thermometer sensors.

2. An electric circuit as claimed in claim 1, wherein the values of the first and second resistances are more than five times the ice point resistance of each of the three resistance thermometer sensors.

3. An electric circuit as claimed in claim 1, wherein the circuit includes means for connecting a direct voltage supply across the bridge circuit and current control means in series with said connecting means and connected to the output of said differential amplifier whereby to control current flowing in said connecting means to said bridge circuit.

4. An electric circuit as claimed in claim 3 wherein the differential amplifier has at least one power supply connection to said connecting means between said current control means and the bridge circuit.

5. An electric circuit as claimed in claim 3 wherein the connecting means includes a pair of terminals for connection to a source of direct voltage, so that the bridge circuit, the differential amplifier, the connecting means and the current control means together constitute a two-wire transmitter.

6. An electric circuit as claimed in claim 5 and including a direct voltage power supply and a current meter in series therewith, remote from said two-wire transmitter, and a two-wire connection from said power supply and current meter to said pair of terminals.

7. An electric circuit as claimed in claim 1 wherein the three resistance thermometer sensors each comprise a conductive platinum rich vitreous film deposited on an insulating substrate.

8. An electric circuit as claimed in claim 1 wherein said first resistance has a value fractionally greater than twice the value of said second resistance.

9. Apparatus for measuring fluid flow rate comprising an electric responsive to changes in the rate of heat loss from a resistance thermometer sensor, the circuit comprising a bridge circuit having first and second arms connected in parallel, the first arm comprising a first resistance thermometer sensor and second and third resistance thermometer sensors connected in parallel with each other and connected at a first balance point in series with said first resistance thermometer sensor, the three resistance thermometer sensors having closely matched values, the second arm comprising first and second resistances connected in series at a second balance point, and a differential amplifier having its inputs connected between the first and second balance points and having its output connected to control current flow in the bridge circuit, the arrangement being such that the differential amplifier is operative to balance the bridge circuit with a finite current flowing in said resistance thermometer sensors, said first resistance having a value fractionally greater than twice the value of said second resistance, and in combination with said electric circuit, means for exposing the three resistance thermometer sensors correspondingly to a flowing fluid of which the rate of flow is to be measured.

10. Apparatus as claimed in claim 9 wherein said means for exposing comprises a rectangular venturi adapted to be located in the fluid steam, the three sensors being mounted so as to be flush with an interior surface of the venturi.

11. Apparatus as claimed in claim 9 wherein the three resistance thermometer sensors each comprise a conductive platinum rich vitreous film deposited on an insulating substrate.

12. Apparatus as claimed in claim 11 wherein the sensors are each formed as an elongate rectangular chip, and said means for exposing comprises a cylindrical venturi, the three sensors being flush mounted side-by-side at circumferentially spaced positions about the interior surface of the venturi, with their major axes aligned with the axis of the venturi.

13. An electric circuit as claimed in claim 1 wherein a third resistance is provided in series with said parallel connected second and third resistance thermometer sensors, the value of said third resistance being a fraction of the ice point resistance value of said second and third resistance thermometer sensors connected in parallel.

14. Apparatus for determining changes in the thermal conductivity of a gas mixture due to changes in composition of the mixture, the apparatus comprising a circuit responsive to changes in the rate of heat loss from a resistance thermometer sensor, the circuit comprising a bridge circuit having first and second arms connected in parallel, the first arm comprising a first resistance thermometer sensor and second and third resistance thermometer sensors connected in parallel with each other and connected at a first balance point in series with said first resistance thermometer sensor, the three resistance thermometer sensors having closely matched values, the second arm comprising first and second resistances connected in series at a second balance point, and a differential amplifier having its inputs connected between the first and second balance points and having its output connected to control current flow in the bridge circuit, the arrangement being such that the differential amplifier is operative to balance the bridge circuit with a finite current flowing in said resistance thermometer sensors, and a third resistance in series with said parallel connected second and third resistance thermometer sensors, the value of said third resistance being a fraction of the ice point resistance value of said second and third resistance thermometer sensors connected in parallel, and in combination with said electric circuit, means for exposing the three resistance thermometer sensors correspondingly to the gas, the values of the first and third resistances being selected to minimise the effect of the temperature coefficient of the thermal conductivity of the gas mixture.

15. Apparatus for determining the thermal conductivity of non-gaseous materials comprising an electric circuit responsive to changes in the rate of heat loss from a resistance thermometer sensor, the circuit comprising a bridge circuit having first and second arms connected in parallel, the first arm comprising a first resistance thermometer sensor and second and third resistance thermometer sensors connected in parallel with each other and connected at a first balance point in series with said first resistance thermometer sensor, the three resistance thermometer sensors having closely matched values, the second arm comprising first and second resistances connected in series at a second balance point, and a differential amplifier having its inputs connected between the first and second balance points and having its output connected to control current flow in the bridge circuit, the arrangement being such that the differential amplifier is operative to balance the bridge circuit with a finite current flowing in said resistance thermometer sensors, and in combination with the electric circuit and elongate probe comprising a hand grip portion and a stem portion extending from the hand grip and having a pointed steel tip, the three resistance thermometer sensors being mounted flush with the surface of the stem near the tip.

* * * * *

UNITED STATES PATENT OFFICE
CERTIFICATE OF CORRECTION

Patent No. 4,080,821      Dated March 28, 1978

Inventor(s) James Stewart Johnston

It is certified that error appears in the above-identified patent and that said Letters Patent are hereby corrected as shown below:

Column 1, line 25, "change" should be --changes--. Column 5, line 54, Equation 1, "$R_1 = 2 R_2 + \alpha R_1$" should be --$R_1 = 2 R_2 + \Delta R_1$--. Column 6, line 34, "$(R_T/R_T)^{1/2}$" should be --$(\Delta R_T/R_T)^{1/2}$--. Column 12, line 47, "and" should be --an--.

Signed and Sealed this

Eighth Day of August 1978

[SEAL]

Attest:

RUTH C. MASON
*Attesting Officer*

DONALD W. BANNER
*Commissioner of Patents and Trademarks*

UNITED STATES PATENT OFFICE
CERTIFICATE OF CORRECTION

Patent No. 4,080,821      Dated March 28, 1978

Inventor(s) James Stewart Johnston

It is certified that error appears in the above-identified patent and that said Letters Patent are hereby corrected as shown below:

Column 8, line 49, $((R_4/2R_3+R_4).\alpha)$ should be

-- $[(R_4/(2R_3 + R_4)].\alpha)$ --.

Signed and Sealed this

Twenty-sixth Day of September 1978

[SEAL]

Attest:

RUTH C. MASON
*Attesting Officer*

DONALD W. BANNER
*Commissioner of Patents and Trademarks*